US011618886B2

(12) United States Patent
Lim et al.

(10) Patent No.: US 11,618,886 B2
(45) Date of Patent: *Apr. 4, 2023

(54) DIFFERENTIATION OF PLURIPOTENT CELLS INTO MICROGLIAL CELLS EXPRESSING IBA-1

(71) Applicant: AGENCY FOR SCIENCE, TECHNOLOGY AND RESEARCH, Singapore (SG)

(72) Inventors: Hwei-In Shawn Lim, Singapore (SG); Tara Huber, Singapore (SG); Florent Ginhoux, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 70 days.

This patent is subject to a terminal disclaimer.

(21) Appl. No.: 16/916,096

(22) Filed: Jun. 29, 2020

(65) Prior Publication Data

US 2020/0399601 A1    Dec. 24, 2020

Related U.S. Application Data

(62) Division of application No. 15/544,254, filed as application No. PCT/SG2016/050018 on Jan. 18, 2016, now Pat. No. 10,724,003.

(30) Foreign Application Priority Data

Jan. 16, 2015    (SG) .......................... 10201500366V

(51) Int. Cl.
| | | |
|---|---|---|
| *C12N 5/00* | (2006.01) | |
| *C12N 5/0786* | (2010.01) | |
| *A61K 35/15* | (2015.01) | |
| *G01N 33/50* | (2006.01) | |

(52) U.S. Cl.
CPC ............ *C12N 5/0645* (2013.01); *A61K 35/15* (2013.01); *G01N 33/5055* (2013.01); *G01N 33/5058* (2013.01); *G01N 33/5073* (2013.01); *C12N 2500/90* (2013.01); *C12N 2501/115* (2013.01); *C12N 2501/125* (2013.01); *C12N 2501/165* (2013.01); *C12N 2501/22* (2013.01); *C12N 2501/2303* (2013.01); *C12N 2501/2306* (2013.01); *C12N 2501/415* (2013.01); *C12N 2501/727* (2013.01); *C12N 2506/02* (2013.01); *C12N 2506/45* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 10,081,792 B2 * | 9/2018 | Thomson ............. | C12N 5/0647 |
| 10,724,003 B2 * | 7/2020 | Lim ....................... | A61P 17/02 |
| 2014/0329321 A1 | 11/2014 | Rajesh et al. | |

FOREIGN PATENT DOCUMENTS

| | | |
|---|---|---|
| JP | 2012519005 A | 8/2012 |
| WO | 2010094734 A2 | 8/2010 |
| WO | 2010099539 A1 | 9/2010 |
| WO | 2012016173 A1 | 2/2012 |
| WO | 2014012933 A1 | 1/2014 |

OTHER PUBLICATIONS

Wikipedia, description for AIF1, 2022.*
The Second Written Opinion for Singaporean Application No. 11201705695Q dated Feb. 10, 2020, 9 pages.
Brown, et al., "The GM-CSF receptor utilizes B-catenin and Tcf4 to specify macrophage lineage differentiation," Differentiation, 2012, pp. 47-59, vol. 83, Elsevier.
The Communication pursuant to Article 94(3) EPC for European Application No. 16737620.1 dated May 29, 2019, 5 pages.
European Patent Office—Extended European Search Report for related European No. 1637620.1, dated May 29, 2016, 7 pages.
The European Office Action for Application No. 16737620.1 dated Oct. 30, 2019, 9 pages.
Furth, Ralph van; et al.; "The Origin and Kinetics of Mononuclear Phagocytes"; The Rockefeller University, New York 10021; published May 3, 1968; 21 pp.
Ginhoux, F., et al., "Fate mapping analysis reveals that adult microglia derive from primitive macrophages." Science, Nov. 5, 2010, American Association for the Advancement of Science USA, vol. 330, No. 6005, pp. 841-845.
Koh, T.J., et al., "Inflammation and wound healing: the role of the macrophage." Expert Reviews in Mol. Med., Jul. 11, 2011, vol. 13, e23: pp. 1-14.
Prinz, M., et al., "Microglia and brain macrophages in the molecular age: from origin to neuropsychiatric disease." Nature Reviews, Neuroscience., Apr. 9, 2014, vol. 15, No. 5, pp. 300-312.
The Office Action for Chinese Application No. 201680006134.1 dated May 6, 2020, 8 pages.
Takata, K., et al. "Induced-Pluripotent-Stem-Cell-Derived Primitive Machrophages Provide a Platform for Modeling Tissue-Resident Macrophage Differentiation and Function." Immunity, Cell Press, Jul. 18, 2017, vol. 47, No. 1, pp. 183.

(Continued)

*Primary Examiner* — Michael C Wilson
(74) *Attorney, Agent, or Firm* — Womble Bond Dickinson (US) LLP

(57) ABSTRACT

The present invention relates to a method of culturing primitive macrophages from stem cells. Specifically, the method comprises contacting and incubating stem cells with a serum-free culture media comprising a GSK3 inhibitor to differentiate stem cells into cell of the mesoderm lineage, contacting and incubating cells of the mesoderm lineage with a culture media comprising DKK1 to differentiate the cells into the hematopoietic lineage, maturing the cells of the hematopoietic lineage and contacting and incubating these cells with a culture media comprising M-CSF to drive differentiation into primitive-like macrophages. The invention also relates to a primitive-like macrophage, use of the primitive-like macrophage and a kit when used in the method of the invention.

3 Claims, 16 Drawing Sheets

(56) References Cited

OTHER PUBLICATIONS

Huber, T.L., "Dissecting hematopoietic differentiation using the embryonic stem cell differentiation model," International Journal of Developmental Biology, 2010, pp. 991-1002, UBC Press.

Paluru, et al., "Clonal genetic and hematopoietic heterogeneity among human-induced pluripotent stem cell lines," Blood, Sep. 19, 2013, pp. 2047-2051, vol. 122, No. 12, The American Society of Hematology.

The Notice of Allowance for U.S. Appl. No. 15/544,254 dated Jul. 29, 2019, 14 pages.

The Notice of Allowance for U.S. Appl. No. 15/544,254 dated Mar. 25, 2020, 6 pages.

The Restriction Requirement for U.S. Appl. No. 15/544,254 dated Oct. 11, 2018, 11 pages.

The Non-Final Office Action for U.S. Appl. No. 15/544,254 dated Feb. 21, 2019, 34 pages.

Communication pursuant to Article 94(3) EPC for EP Application No. 16737620.1 dated Oct. 30, 2019, 9 pages.

Notification of Reasons for Refusal for Japanese Patent Application No. 2017-536895 dated Jan. 27, 2020, 11 pages, [English Translation].

IP Office of Singapore; Notification of Transmittal of The International Search Report and The Written Opinion of the International Searching Authority, or The Declaration for counterpart International Application No. PCT/SG2016/050018 containing International Search Report and Written Opinion, dated Apr. 21, 2016, 14 pages.

Brandon C. et al, "WNT signaling modulates the diversification of hematopoietic cells," Hematopoiesis, Dec. 15, 2000, vol. 96, No. 13, pp. 4132-4141.

Kirstetter P. et al, "Activation of the Canonical WNT Pathway Leads to the Loss of Hematopoietic Stem Cell Repopulation and Multi-lineage Differentiation." Nature Immunology, Sep. 3, 2006, vol. 7, pp. 1048-1056.

Tan J.Y. et al, "Efficient Derivation of Lateral Plate and Paraxial Mesoderm Subtypes from Human Embryonic Stem Cells Through GSKi-Mediated Differentiation," Stem Cells and Development, Feb. 15, 2013, vol. 22, No. 13, pp. 1893-1906 Singapore.

Rai M. et al, Continuous antagonism by Dkk1 counter activates canonical WNT Signaling and Promotes Cardiomyocyte Differentiation of Embryonic Stem Cells. Stem Cells and Development, Oct. 18, 2011, vol. 21, No. 1, pp. 54-66. Tennessee.

Lu S-J. et al, GeneChip Analysis of Human Embryonic Stem Cell Differentiation into Hemangioblasts: An in silica Dissection of Mixed Phenotypes, Genome Biology, Nov. 13, 2007, vol. 8, No. 11, Article R240, pp. 1-19. USA.

Hoeffel et al., "Adult Langerhans cells derive predominantly from embryonic fetal liver monocytes with a minor contribution of yolk sac-derived macrophages", Journal of Experiential Medicine, vol. 209, No. 6, May 7, 2012, pp. 11670-1181.

International Preliminary Report on Patentability dated Jul. 18, 2017, for PCT application No. PCT /SG2016/050018.

The Communication pursuant to Article 94(3) EPC for Application No. 16373620.1 dated May 27, 2020, 4 pages.

* cited by examiner

Neuron (Tuj-1)/ Macrophage (Iba1)/ Nuclei (Hoechst)

Accumulation of Surfactant Associated Protein B (SPB)

SiglecF

DIFFERENTIATION OF PLURIPOTENT CELLS INTO MICROGLIAL CELLS EXPRESSING IBA-1

CROSS-REFERENCE TO RELATED APPLICATIONS

This patent application is a divisional application of a U.S. patent application Ser. No. 15/544,254, filed on Jul. 17, 2017, which is a U.S. National Phase application under 35 U.S.C. § 371 of International Application No. PCT/SG2016/050018, filed on Jan. 18, 2016, entitled DIFFERENTIATION OF MACROPHAGES FROM PLURIPOTENT STEM CELLS, which claims the benefit of priority of Singapore application number 10201500366V, filed Jan. 16, 2015, the contents of which were hereby incorporated by reference in the entirety for all purposes.

FIELD OF THE INVENTION

The invention relates to a differentiation of macrophages from stem cells. Specifically, the invention relates to a serum-free, feeder-free and embryoid body-free method for differentiation of primitive macrophages from stem cells.

BACKGROUND OF THE INVENTION

Macrophages are mononuclear phagocytes that play a crucial role in tissue homeostasis and immunity, but also contribute to a broad spectrum of pathologies and thus represent key therapeutic targets. However, in depth insights into the differentiation of primitive macrophages from human pluripotent stem cells, their homeostasis, as well as their defined activities in a tissue-specific context are currently lacking.

According to the mononuclear phagocyte system (MPS) concept, homeostasis of tissue resident macrophages relies on the constant recruitment of blood monocytes. However, while monocytes clearly give rise to macrophages in pathological settings and inflammation, recent evidence has shown that (1) monocytes do not substantially contribute to certain tissue macrophages under steady state and in certain types of inflammation, and (2) some adult tissue macrophages such as brain microglia are derived from embryonic primitive precursors called primitive macrophages that seed tissues prior to birth and maintain themselves in adults by self-renewal.

Based on this evidence, there is a need to recapitulate the embryonic primitive origin of macrophages in vitro in order to design new clinical strategies targeted to monocytes and macrophages. In this regard, the vast majority of existing approaches to hematopoietic differentiation of human cells have utilized either co-culture with a stromal layer, or as embryoid bodies (EBs). Many of these protocols rely on the use of an undefined bovine serum supplement. These conditions introduce intrinsic levels of variability into protocols for hematopoietic differentiation of human cells that can affect reproducibility and yields. Accordingly, there is a need to provide a method for hematopoietic differentiation that overcomes, or at least ameliorates, one or more of the disadvantages described above to recapitulate the embryonic origin of macrophages in vitro.

SUMMARY OF THE INVENTION

In one aspect, there is provided a method for culturing primitive-like macrophages from stem cells wherein the method comprises:

(a) contacting and incubating said stem cells with a serum-free culture media comprising a GSK3 inhibitor to induce differentiation of said stem cells into cells of the mesoderm lineage;

(b) contacting and incubating said cells of the mesoderm lineage with a culture media comprising DKK1 to differentiate the cells of the mesoderm lineage into cells of the hematopoietic cell lineage;

(c) maturing said cells of the hematopoietic cell lineage;

(d) contacting and incubating said mature cells of the hematopoietic cell lineage with a culture media comprising M-CSF to drive the differentiation of said hematopoietic cells into primitive-like macrophages.

In one aspect, there is provided a kit when used in the method as defined herein, comprising a GSK3 inhibitor and DKK1 with instructions for use.

In one aspect, there is provided a primitive-like macrophage obtained by the method as described herein.

In one aspect, there is provided a use of the primitive-like macrophage as described herein for developing in vitro disease models, wherein the disease is a neurodegenerative disease, a metabolic disease, a respiratory disease, a cardiovascular disease, a connective tissue disease, cancer or an inflammatory disease.

In one aspect, there is provided a use of the microglial cell as described herein for developing in vitro disease models, wherein the disease is a neurodegenerative disease.

In one aspect, there is provided a use of the primitive-like macrophage as described herein for screening compounds to treat a disease, wherein the disease is a neurodegenerative disease or a metabolic disease.

In one aspect, there is provided a use of the microglial cell as described herein for screening compounds to treat a disease, wherein the disease is a neurodegenerative disease.

In one aspect, there is provided a use of the primitive-like macrophage as described herein for in the manufacture of a medicament for wound healing and tissue regeneration.

In one aspect, there is provided a use of the primitive-like macrophage as described herein for delivering a cargo molecule into a tissue, wherein the cargo molecule is an immunomodulatory cytokine or chemokine, or an enzyme that activates pro-drugs.

In one aspect, there is provided a method for culturing primitive-like macrophages from murine stem cells wherein the method comprises:

(a) contacting and incubating said stem cells with a serum-free culture media comprising FGF2 and BMP4 to induce differentiation of said stem cells into cells of the mesoderm lineage;

(b) contacting and incubating said cells of the mesoderm lineage with a culture media comprising FGF2, BMP4, Activin A and VEGF to differentiate the cells of the mesoderm lineage into cells of the hematopoietic cell lineage;

(c) maturing said cells of the hematopoietic cell lineage;

(d) contacting and incubating said mature cells of the hematopoietic cell lineage with a culture media comprising M-CSF to drive the differentiation of said hematopoietic cells into primitive-like macrophages.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE PRESENT INVENTION

Figure 1:
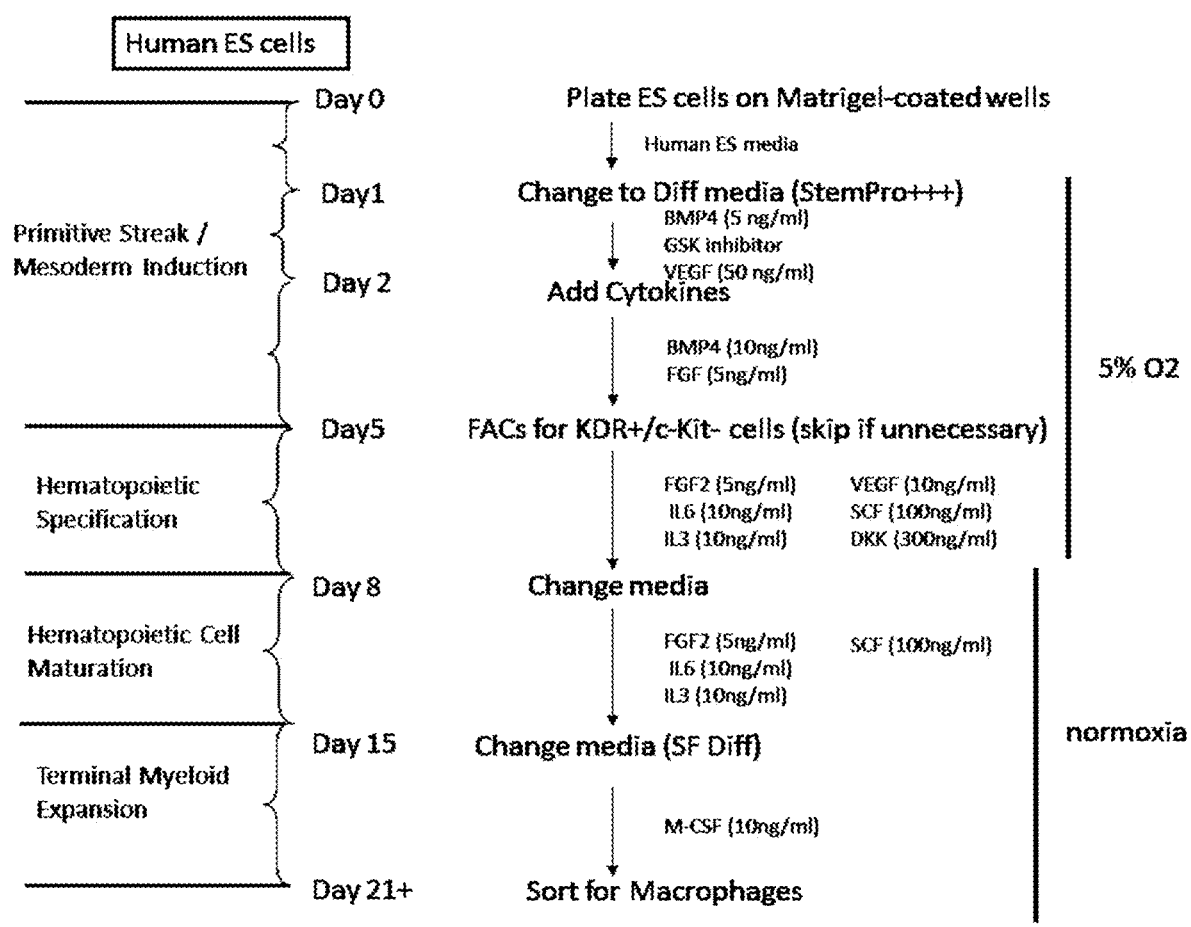
FIG. 1 shows a flow diagram of the method of the invention.

In a first aspect the present invention refers to a method for culturing primitive-like macrophages from stem cells. The method comprises: (a) contacting and incubating said stem cells with a serum-free culture media comprising a GSK3 inhibitor to induce differentiation of said stem cells into cells of the mesoderm lineage; (b) contacting and incubating said cells of the mesoderm lineage with a culture media comprising DKK1 to differentiate the cells of the mesoderm lineage into cells of the hematopoietic cell lineage; (c) maturing said cells of the hematopoietic cell lineage; and (d) contacting and incubating said mature cells of the hematopoietic cell lineage with a culture media comprising M-CSF to drive the differentiation of said hematopoietic cells into primitive-like macrophages.

The stem cells may be selected from embryonic stem cells (ESC) and induced pluripotent stem cells (iPSC). In one embodiment the stem cells may be human H1 embryonic stem cells (ESC). In another embodiment the stem cells may be human induced pluripotent stem cells (iPSC).

The GSK3 inhibitor may be selected from 6-bromoindirubin-3'-oxime (BIO), CHIR-99021, SB216763, CHIR-98014, TWS119, IM-12, 1-Azakenpaullone, AR-A014418, SB415286, AZD1080, AZD2858, indirubin, A 1070722, TCS 2002, Tideglusib, or any derivatives thereof.

In some embodiments the stem cells may be plated at a density of less than 1 small colony/cm$^2$ on Matrigel-coated 6-well plates at least 24 hours prior to step (a).

The stem cells may be incubated with a media comprising 80% DMEM/F12, 20% knockout serum replacement, L-glutamine, non-essential amino acids, beta-mercaptoethanol and FGF-2, step (a). In some embodiments, the stem cells may be incubated for about 1 day in said media.

In another embodiment, the stem cells may be contacted at step (a) with a differentiation media, comprising 1-20 ng/ml of BMP4, 5-100 ng/ml of VEGF, 0-50 ng/ml of FGF-2, and 0-10 μM of CHIR99021. The differentiation media may be StemPro® 34 from Invitrogen. The cells may be incubated with the media for about 2 days in an oxygen concentration of about 5%.

In another embodiment, the cells are further contacted at step (a) with 1-20 ng/ml of BMP4 and 5-100 ng/ml of VEGF.

In another embodiment, the cells are incubated for about 2 days with said media in an oxygen concentration of about 5%.

The cells may be contacted at step (b) with a differentiation media comprising 5-100 ng/ml of VEGF; 0-50 ng/ml of FGF-2; 0-250 ng/ml of SCF; 0-500 ng/ml DKK1; 0-50 ng/ml of IL-6; and 0-50 ng/ml of IL-3. The cells may be incubated for about 3 days with said media in an oxygen concentration of about 5%.

In some embodiments, the cells at step (c) may be matured by contact with a differentiation media comprising 0-50 ng/ml of FGF-2; 0-250 ng/ml of SCF; 0-50 ng/ml of IL-3 and 0-50 ng/ml of IL-6. The cells may be incubated with the media for about 7 days in normoxic conditions. The term "normoxic conditions" as used herein refers to conditions where the oxygen concentration levels may be about 20% in the media.

The cells may be contacted and incubated at step (d) with a differentiation media comprising 0-100 ng/ml M-CSF. The cells may be incubated with the media for at least 6 days in normoxic conditions.

In one embodiment the method as described herein may produce a yield of primitive-like macrophages of greater than $1 \times 10^6$/well in a 6-well culture plate between 21 to 25 days of culture. As will be appreciated in the art, the yield of the macrophages may be dependent upon the origin of the cells that are applied in the methods described herein.

In another embodiment the method may further comprise isolating said primitive-like macrophages using FACS sorting or magnetic separation.

Also provided herein is a kit when used in accordance with the method as described herein, comprising a GSK3 inhibitor and DKK1 with instructions for use.

Also provided herein is a primitive-like macrophage obtained by the method as described herein. The primitive-like macrophage may be subsequently differentiated into a microglial cell, an alveolar macrophage, Kupffer cell, Langerhans cell, or other tissue macrophages. The term "macrophages of other tissues" refers to macrophages that may be found in any tissue type including but not limited to kidney tissue, pancreas tissue, adipose tissue, liver tissue or connective tissue.

Also provided herein is the use of the primitive-like macrophage as described herein for developing in vitro disease models, wherein the disease is a neurodegenerative disease, a metabolic disease, a respiratory disease, a cardiovascular disease, a connective tissue disease, cancer or an inflammatory disease. In one embodiment the disease is a neurodegenerative disease.

In some embodiments, there is provided use of the primitive-like macrophage as described herein for screening compounds to treat a disease, wherein the disease is a neurodegenerative disease or a metabolic disease.

In some embodiments, the disease is a neurodegenerative disease. In some embodiments, the neurodegenerative disease may be Alzheimer's disease, Huntington's disease or Rett syndrome. In some embodiments, the metabolic disease may be obesity or diabetes. In some embodiments, the respiratory disease may be pulmonary alveolar proteinosis. In some embodiments, the cardiovascular disease may be atherosclerosis. In some embodiments, the connective tissue disease may be fibrosis. In some embodiments the inflammatory disease may be arthritis, rheumatoid arthritis, experimental autoimmune encephalomyelitis, multiple sclerosis or inflammatory bowel disease as well as skin inflammatory disease such as Atopic Dermatitis, Psoriasis.

There is also provided the use of the primitive-like macrophage as described herein for wound healing and tissue regeneration.

There is also provided the use of the primitive-like macrophage as described herein for delivering a cargo molecule into a tissue, wherein the cargo molecule is an immunomodulatory cytokine or chemokine, or an enzyme that activates pro-drugs.

There is also provided a method for culturing primitive-like macrophages from murine stem cells wherein the method comprises: (a) contacting and incubating said stem cells with a serum-free culture media comprising FGF2 and BMP4 to induce differentiation of said stem cells into cells of the mesoderm lineage; (b) contacting and incubating said cells of the mesoderm lineage with a culture media comprising FGF2, BMP4, Activin A and VEGF to differentiate the cells of the mesoderm lineage into cells of the hematopoietic cell lineage; (c) maturing said cells of the hematopoietic cell lineage; (d) contacting and incubating said mature cells of the hematopoietic cell lineage with a culture media comprising M-CSF to drive the differentiation of said hematopoietic cells into primitive-like macrophages.

The murine stem cells may be selected from mouse embryonic stem cells (ESC) and mouse induced pluripotent stem cells (iPSC).

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention, including the best mode, and a comparative example will be further described in greater detail by reference to specific Examples, which should not be construed as in any way limiting the scope of the invention.

Example 1

Differentiation of Mouse Pluripotent Stem Cells into Primitive Macrophages

If mESC/miPSC are expanded on MEF, deplete MEF by 1-2× passage on gelatin-coated 6-well plates before commencing with differentiation.

On day 0, colonies are dissociated and resuspended at 175,000-200,000 cells/ml in serum-free differentiation medium (recipe below) supplemented with 5 ng/ml hFGF2 and 5 ng/ml hBMP4. These are dispensed into non-adherent plates to allow for embryoid body (EB) formation.

After 48 h, EBs are pooled and dissociated with TrypLE (preferred) or Trypsin.

EBs are then reaggregated at 175,000 cells/ml in serum-free differentiation medium supplemented with 5 ng/ml hFGF2, 2 ng/ml hBMP4, 2 ng/ml human Activin A, 5 ng/ml hVEGF.

After a further 48 h, EBs are dissociated and sorted for Flk-1+ cells.

Sorted cells are then reaggregated at 500,000 cells/ml in serum-free differentiation medium supplemented with 5 ng/ml VEGF, 300 ng/ml DKK1, 100 ng/ml M-CSF. The cell suspension is then dispensed into non-adherent culture wells to allow EB formation.

After a further 48 h (d6 of differentiation total), EBs are dissociated and resuspended in StemPro SFM complete medium (recipe below) supplemented with 100 ng/ml SCF, 10 ng/ml IL-3, 100 ng/ml M-CSF. The cells are then plated onto gelatin-coated tissue culture plates.

Primitive-like macrophages should emerge starting from d8 of differentiation and peak around d13-14 of differentiation. Typically cells are sorted or harvested around d10-11. It is not necessary to passage the cells, but note that there will be many cells in suspension by d8. Collect both suspension and adherent fractions for sorting.

Serum-Free Differentiation Medium:
75% IMDM/25% F12
0.5×N2 supplement
0.5×B27 supplement (without retinoic acid)
1× pen/strep
0.05% BSA
2 mM L-glutamine
0.5 mM ascorbic acid
$4.5 \times 10^{-4}$ M 1-thioglycerol StemPro SFM Complete Medium:
StemPro-34 SFM (Invitrogen)
1× pen/strep
2 mM L-glutamine
200 ug/ml transferrin
0.5 mM ascorbic acid
$4.5 \times 10^{-4}$ M 1-thioglycerol

Example 2

Differentiation of Human Pluripotent Stem Cells into Primitive Macrophages

Figure 2:
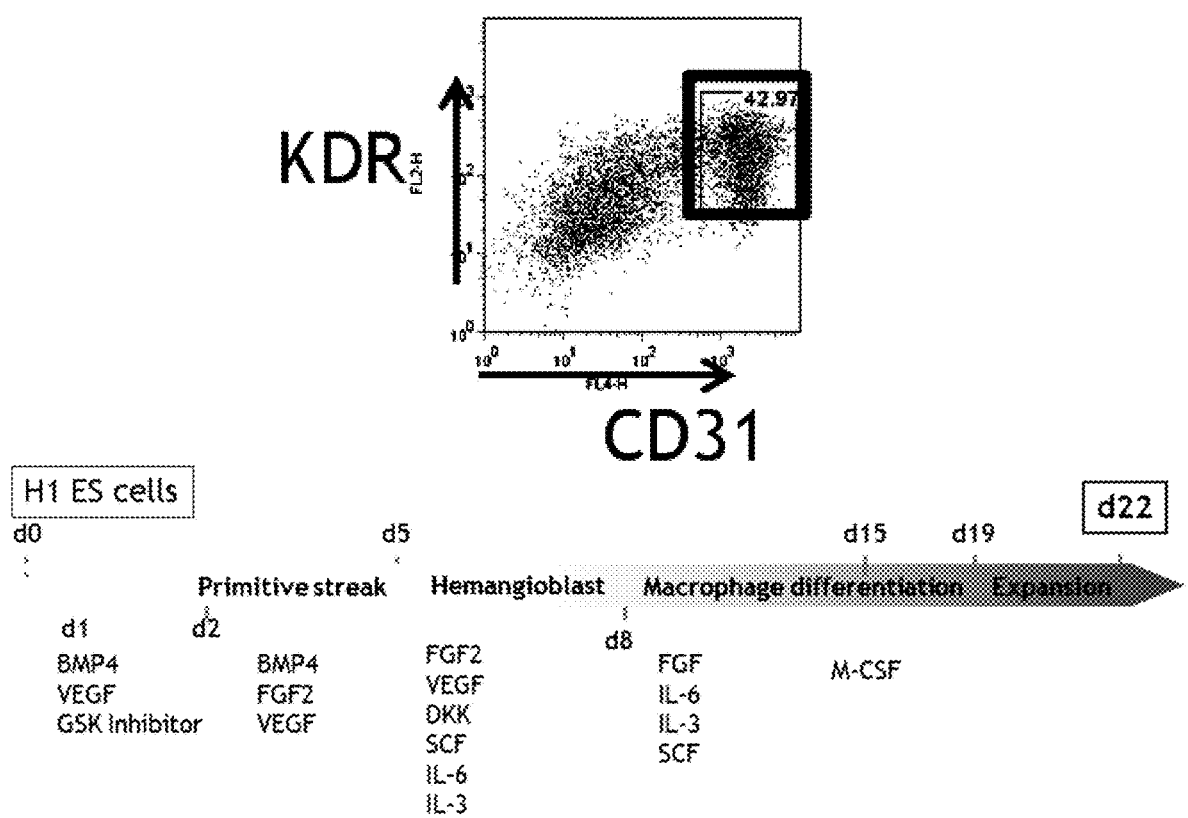
FIG. 2 shows the timeline for the addition of growth factors used in the method of the invention.

The differentiation strategy can be divided into four stages: primitive streak/mesoderm induction, hematopoietic specification, hematopoietic cell maturation, and finally terminal myeloid expansion. The experimental details of each stage are illustrated in FIGS. 1 and 2, and described below:

Stage 0: ES or iPS cells are maintained on Matrigel-coated dishes in CF1 MEF-conditioned media. The media recipe consists of 80% DMEM/F12, 20% knockout serum replacement, L-glutamine, non-essential amino acids, beta-mercaptoethanol, and 6 ng/ml FGF-2 and media is replaced daily. Cells are passaged every 5-6 days using collagenase IV treatment and gentle detachment with a cell scraper. 24 hours prior to initiation of differentiation, cells are plated at a very low density (<1 small colony/cm² on Matrigel-coated 6-well plates and allowed to attach overnight.

Stage 1 (primitive streak/mesoderm induction): In this initial stage, cells are treated with BMP4 and GSK3 inhibitor to promote specification to the posterior primitive streak, which gives rise to the mesoderm during embryogenesis. VEGF is also added to promote the development of hematopoietic mesoderm. The cells are also maintained under hypoxic conditions (5% $O_2$).

Stage 2 (hematopoietic specification): After approximately 4-5 days, a subset of cells with high expression of KDR and CD31 can be observed. This population contains the hemangioblast, the bipotential precursor to hematopoietic and endothelial cells. The induction cocktail at this point is tailored to expand hemangioblast cells and further specify them towards the hematopoietic lineage. Here, SCF and FGF-2 are added to promote cell viability and proliferation. IL-3, IL-6 and VEGF are added to promote hematopoietic differentiation, and DKK1 is added to suppress erythroid differentiation (and perhaps drive macrophage differentiation). Cells are maintained in hypoxic conditions until day 8, after which they are cultured in normoxia.

Stage 3 (Hematopoietic cell maturation): In this stage, hematopoietic cells are driven more fully towards the macrophage lineage. DKK and VEGF are no longer necessary by this point and are thus removed from the cocktail.

Stage 4 (terminal myeloid expansion): All cytokines are removed with the exception of M-CSF, which was found to promote the proliferation of primitive macrophages via signaling through the CSF1-receptor.

Figure 3A:
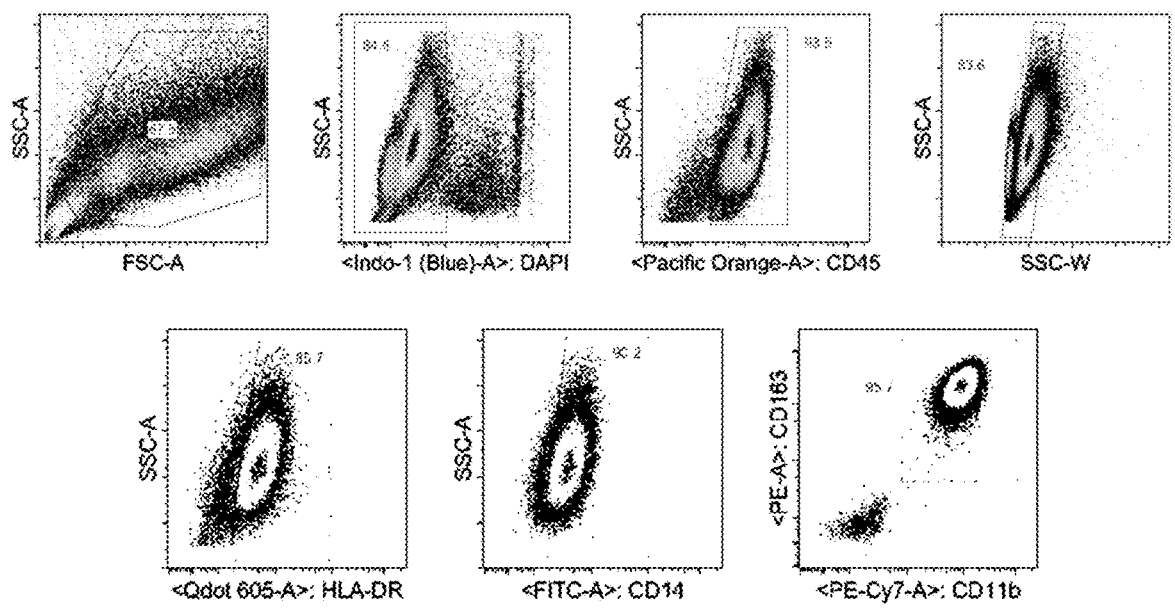
FIGS. 3A-3C show the flow cytometry analysis of macrophages differentiated from H1 ES cells (FIG. 3A), patient-derived WT iPSCs (FIG. 3B) and patient-derived mutant iPSCs (FIG. 3C): Cells are sequentially gated on their FSC/SSC profile, then live cells (DAPI−), then hematopoietic cell (CD45+) and then singlets (SSC-A and SSC-W gate). Profile of expression of common macrophage markers are shown: CD14, HLA-DR, CD11b and CD163. Macrophages differentiated from H1 ES cells, patient derived WT iPSCs and patient-derived mutant iPSCs are CD14+, HLA-DR+ and most of them CD163+ and CD11b+. (SSC=side scatter: Side scatter measures scattered light at 90 degrees to the laser path and measures the granularity of the cell; FSC=Forward Scatter: Forward scatter measures scattered light in the direction of the laser path and measures the size of the cell; DAPI (4',6-Diamidino-2-phenylindole dihydrochloride): CD45: Pan hematopoietic cell marker; HLA-DR: Macrophage and dendritic cell marker, MHC class II cell surface receptor encoded by the human leukocyte antigen complex; CD14: cluster of differentiation 14, Macrophage marker; CD11b: Integrin alpha M (ITGAM), Macrophage marker; CD163: cluster of differentiation 163, high affinity scavenger receptor for the hemoglobin-haptoglobin complex, Macrophage marker).
Figure 3B:
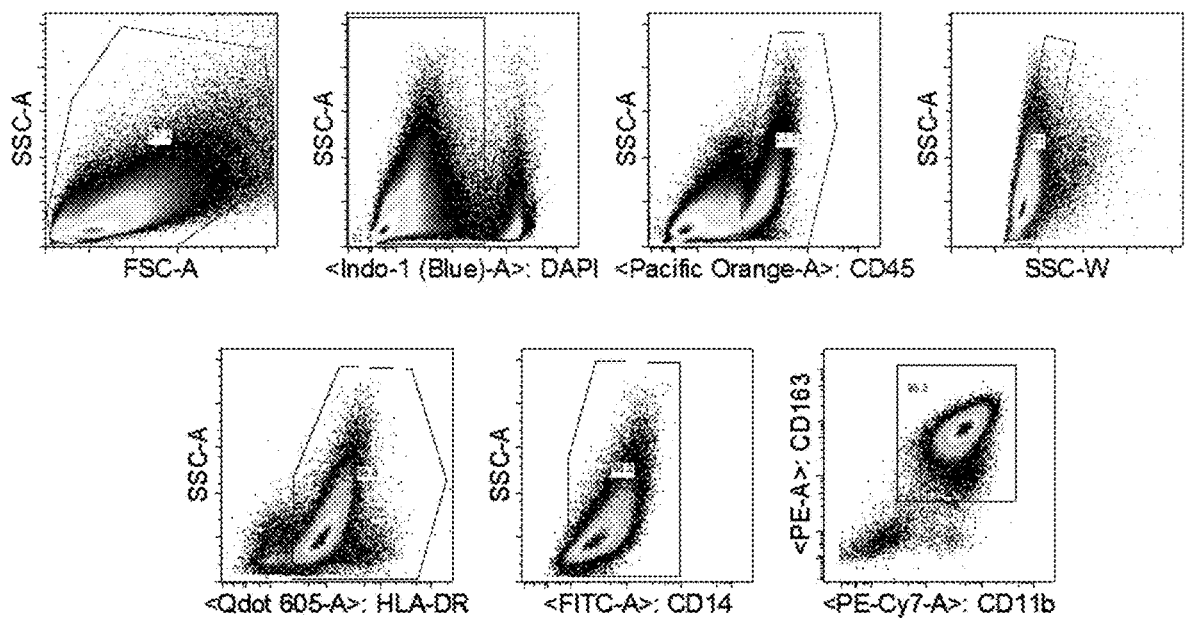
Figure 3C:
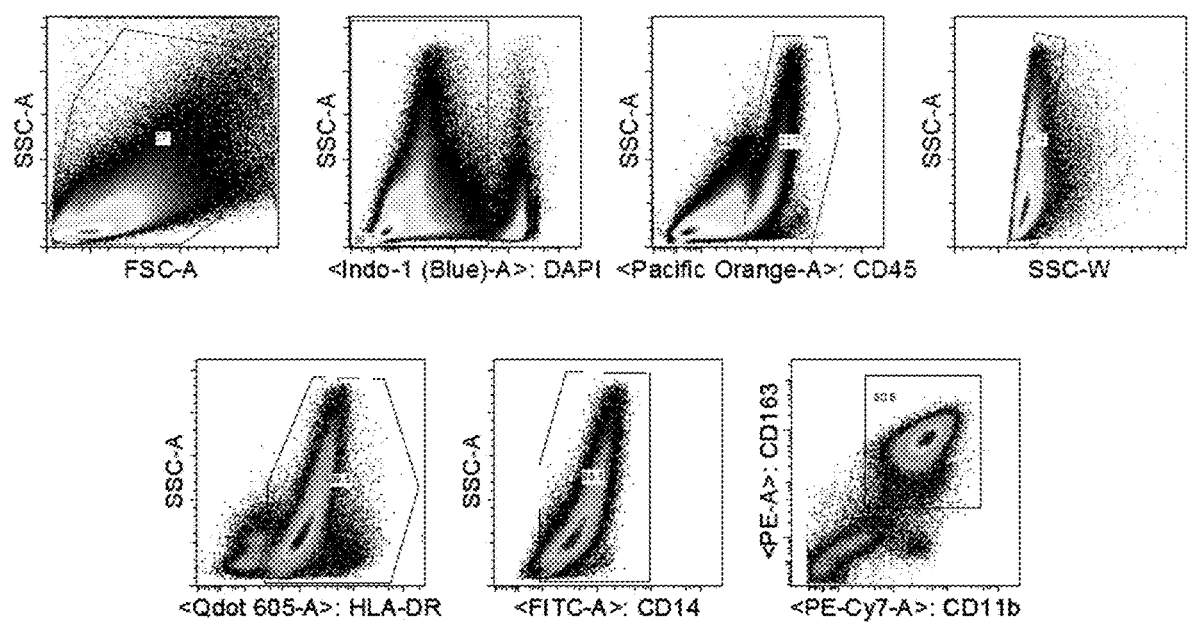

Macrophages expressing classical surface markers can be observed in the populations as early as day 18 of differentiation, and we have found that flow sorting of cells between day 21-25 of differentiation results in good yield and viability. Specifically, the expression profile of common macrophage markers (CD14, HLA-DR, CD11b and CD163) are shown in FIG. 3 with respect to macrophages differentiated from H1 ES cells, patient derived WT iPSCs and patient-derived mutant iPSCs.

Differentiation Medium 1 (DM1)
StemPro 34 (Invitrogen) with the supplement and 1× pen/strep
2 mM glutamine
1× apo-transferrin
$4 \times 10^{-4}$ M monothioglycerol (MTG)
50 ug/ml ascorbic acid (AA)
Differentiation Medium 2 (DM2)
IMDM 75%/Ham's F-12 25% with 1× pen/strep
0.5×B27 supplement (without retinoic acid)
0.5×N2 supplement
2 mM glutamine
$4 \times 10^{-4}$ M monothioglycerol
50 ug/ml ascorbic acid
Procedure
Day 0: Exchange expansion media with DM1 containing BMP4 (5 ng/ml), VEGF (50 ng/ml), CHIR99021 (2 µM). Culture in 5% $O_2$.
Day 2: Exchange media with DM1 containing BMP4 (5 ng/ml), VEGF (50 ng/ml), FGF-2 (20 ng/ml). Culture in 5% $O_2$.
Day 4: Exchange media with DM1 containing VEGF (15 ng/ml), FGF-2 (5 ng/ml). Culture in 5% $O_2$.

Day 6: Exchange media with DM1 containing VEGF (10 ng/ml), FGF-2 (10 ng/ml), SCF (50 ng/ml), DKK1 (30 ng/ml), IL-6 (10 ng/ml), IL-3 (20 ng/ml). Culture in 5% $O_2$.

Day 8, 10: Exchange media with DM1 containing VEGF (10 ng/ml), FGF-2 (10 ng/ml), SCF (50 ng/ml), DKK1 (30 ng/ml), IL-6 (10 ng/ml), IL-3 (20 ng/ml). Return cells to normoxic conditions (20% $O_2$).

Day 12, 14: Exchange media with DM1 containing FGF-2 (10 ng/ml), SCF (50 ng/ml), IL-6 (10 ng/ml), IL-3 (20 ng/ml).

Day 16, 18, 20: Exchange media with DM2 containing MCSF (50 ng/ml).

Technical Notes

A volume of 3 ml media/well in the 6 well plate is recommended.

From day 6 onwards, cells in suspension are observed. To avoid loss of hematopoietic cells, the supernatant is centrifuged and the resultant cell pellet is re-suspended in a small quantity of fresh media before being added back to their original wells.

DM1 should be freshly prepared every 5-7 days and stored at 4° C. to minimize loss of bioactivity.

DM2 can be prepared (without AA and MTG) in advance and frozen in aliquots before use. AA and MTG can be added to thawed aliquots and stored for up to one week at 4° C.

There are a number of unique and advantageous features of this method including that it mimics primitive hematopoiesis in the embryonic yolk sac. This method is completely serum- and feeder-free, as compared to competing technologies that require serum supplementation later on and that require co-culture with stromal cells such as OP9. In addition, no dissociation steps are required and there is no embryoid body formation stage. Rather, differentiation takes place on 2D adherent culture over the entire process. The method has also been validated on H1 cells and other iPSC cell lines and is scalable, resulting in high yield of primitive macrophages ($>1\times10^6$/well in a 6 well plate). The addition of the GSK inhibitor pushes initial specification towards the primitive streak while the addition of DKK suppresses erythroid differentiation.

Example 3

Differentiation of Human iPSC-Derived Primitive Macrophages

Phagocytosis assays were performed with day 12-sorted iPSCs-derived primitive macrophages (CD163+CD11b+ HLA-DR+IBA-1+CX3CR1+CD14+), wherein the macrophages have been differentiated from patient derived WT iPSCs and the expression profile is CD45+CD11b+, and CD163+. Specifically, the day 12-sorted iPSCs-derived primitive macrophages were exposed to fluorescently labeled latex beads or amyloid Aβ peptides in order to assess their capacity to phagocyte as macrophages and microglia.

Figure 4:
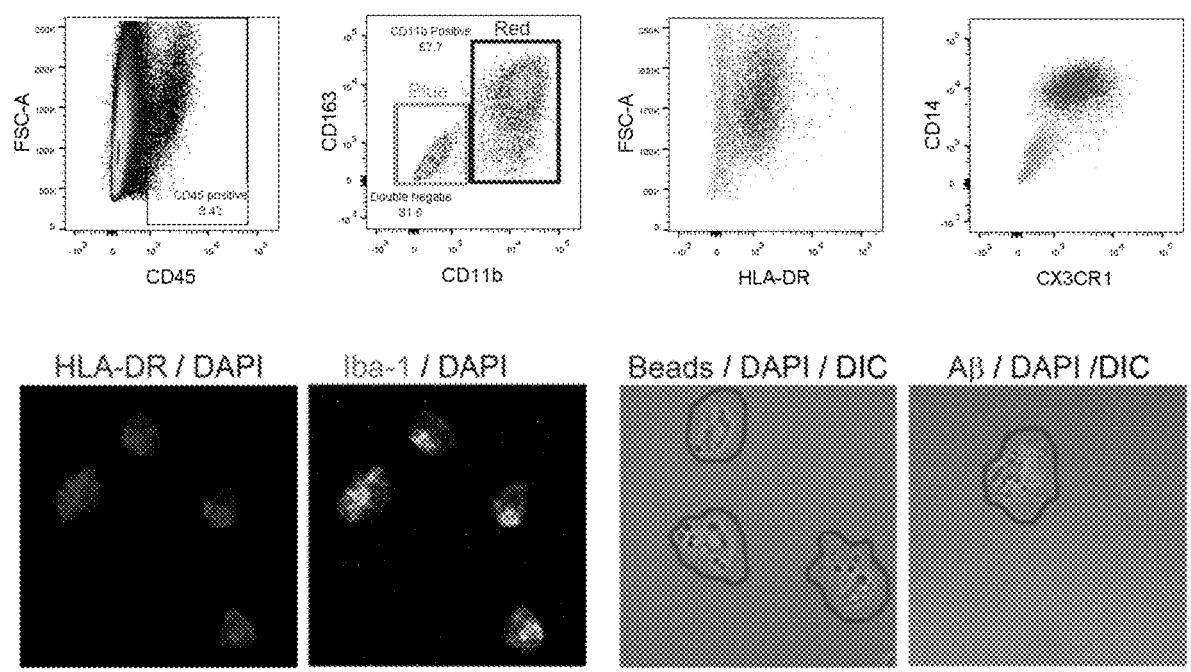
FIG. 4 shows the results of phagocytosis assays on day 12-sorted iPSCs-derived primitive macrophages when exposed to fluorescently labeled latex beads or amyloid Aβ peptides. IBA-1=ionized calcium-binding adapter molecule 1 (Microglia and macrophage marker); CX3CR1= fractalkine receptor; DIC=Differential interference contrast.

As shown in FIG. 4, the capacity of said iPSC-derived primitive macrophages to phagocyte as macrophages and microglia is supported. This is of importance since amyloid beta (Aβ or Abeta) peptides are crucially involved in Alzheimer's disease as the main component of the amyloid plaques found in the brains of Alzheimer patients.

Procedure

The method for the analysis of macrophage phagocytic ability used a control line of Huntington's disease human iPSCs (HD33i) derived primitive macrophages that were reconstituted with IMDM containing 10% FCS, seeded ($5.0\times10^4$ cells/well) on the 24-well-dish, and settled overnight at 37° C. in a fully humidified atmosphere of 5% CO2 in air.

Cells were then incubated with latex beads (1:100,000) for 24 hours, washed with PBS three times, fixed with 4% PFA, and analyzed by laser confocal microscopy.

Phagocytosed latex beads were analyzed by the reference of cell morphology (differential interference contrast) and nuclei (DAPI, 1:10,000).

Example 4

Human iPSC Derived Neuron and Macrophage Co-Culture.

iPSC-derived primitive macrophages obtained from the methods described herein were co-cultured with neurons.

Figure 5:
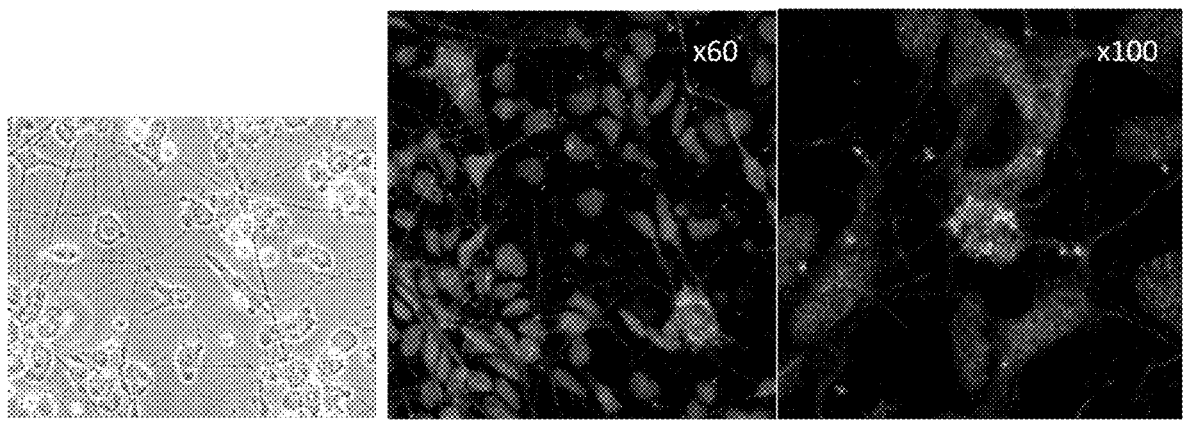
FIG. 5 shows microscope images of the results from the co-culture of iPSC-derived primitive macrophages on neurons after 7 days of culture. Tuj1=neuron-specific class III beta-tubulin marker; Iba1=ionized calcium-binding adapter molecule 1 (Microglia and macrophage marker); Hoechst=Fluorescent dye that labels DNA and then the nucleus of cells. The number in the top right of the images (*60 and *100) indicate microscope magnification.
Figure 6:
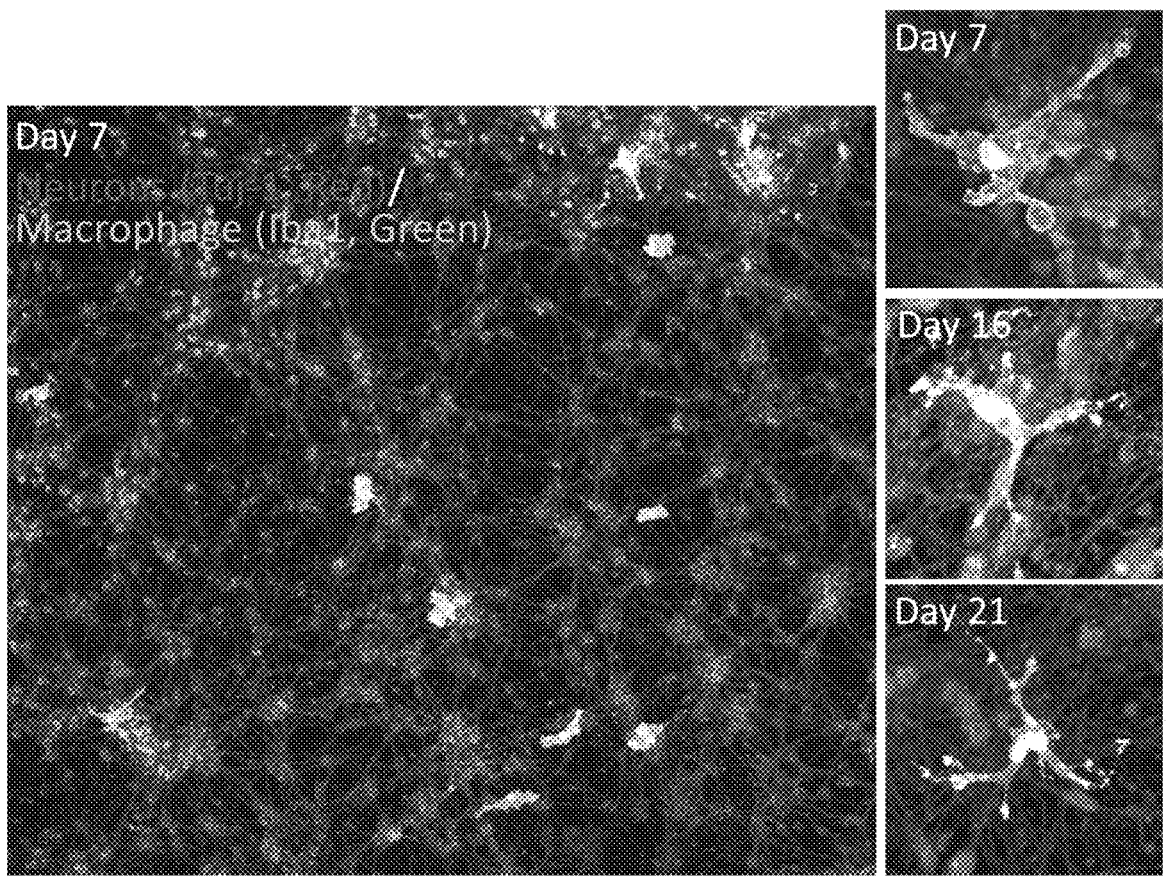
FIG. 6 shows microscope images of the results from the co-culture of iPSC-derived primitive macrophages on iPSC-derived neurons (Same source of iPSC) at different days (7, 16 and 21) of co-culture.

As shown in FIGS. 5 and 6, the co-culture led to the differentiation of the iPSC-derived primitive macrophages into IBA1+ microglia with a ramified morphology reminiscent of in vivo adult microglia.

These results show that iPSC-derived primitive macrophages have the capacity to differentiate into microglial cells.

Procedure

Differentiation methods described herein were adopted to induce the neurons from human iPSCs (HD33i). Eighty percent (80%) confluency of iPSCs were washed with DMEM/F12 two times and dissociated to single cells with accutase. Cells were re-suspended with neuron precursor cell (NPC)+ medium and plated on the matrigel coated 6-well-dish. NPC+ medium was changed every day for 7 days for the induction of NPCs. NPCs were then split at 1:3 dilution in NPC− medium with 10 µM ROCK inhibitor on the matrigel coated 6-well-dish and followed by several passages for the conditioning with NPC− media supplemented with EGF (20 ng/ml) and bFGF (20 ng/ml). For the terminal differentiation to neurons, confluent NPCs were dissociated to single cells with accutase, re-suspended with neuron differentiation medium, and seeded ($5.0\times10^4$ cells/well) on the coverslip coated with poly-L-ornithine and laminin in 24-well-dish.

Example 5

CSF2aR-KO Mice Lung-Transplantation

A CSF2aR-KO Mice (CD45.2) mouse model of Pulmonary Alveolar Proteinosis was used in testing the effect of iPSC-derived primitive macrophages.

Figure 7:
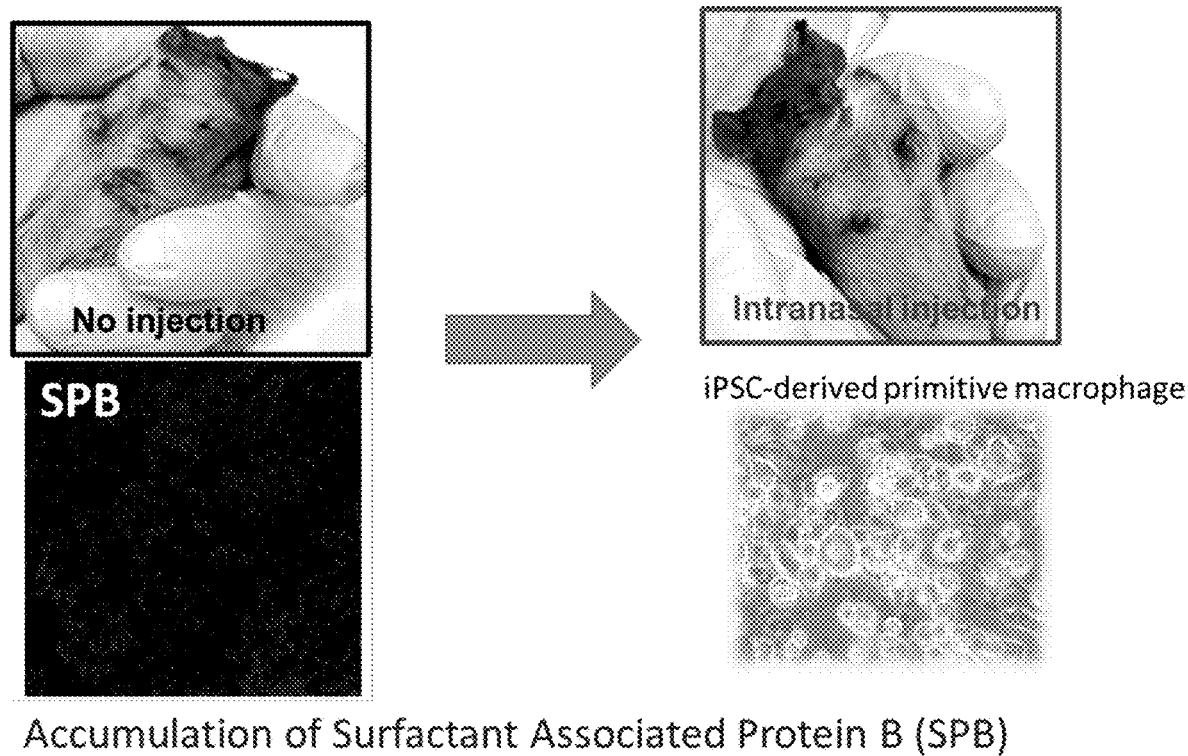
FIG. 7 shows an illustration of the strategy of transferring murine iPSC-derived primitive macrophages intranasally on the CSF2aR-KO Mouse (CD45.2) model in order to test their function.

As shown in FIG. 7, the transfer of murine iPSC-derived primitive macrophages rescued and alleviated the Pulmonary Alveolar Proteinosis disease in the mouse model.

Cell suspensions from the lung of non-treated wild type mouse (8a, positive control), the non-treated mouse model CSF2aR-KO (8b, negative control) and the mouse model CSF2aR-KO with added iPSC macrophages in the cell suspension as a technical control (8c) were analysed through flow cytometry and the presence or absence of alveolar macrophages detected through the visualisation of known macrophage markers.

Figure 8A:
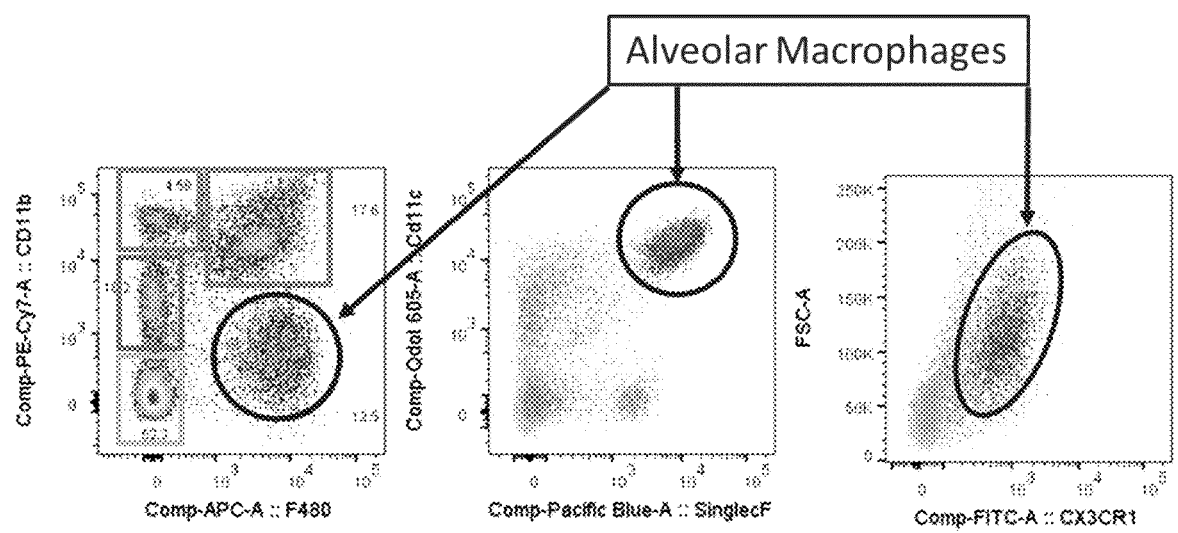
FIGS. 8A-8C show the flow cytometry analysis of a wild type (WT) Mouse's lung (8-month-old) (FIG. 8A); CSF2aR-KO Mouse lung (9-month-old) (FIG. 8B), where no alveolar macrophages are shown (differentiation defect); and CSF2aR-KO Mouse's lung (1.5-month-old) (FIG. 8C)+ Positive Control (Frozen iPSC Macrophage).
Figure 8B:
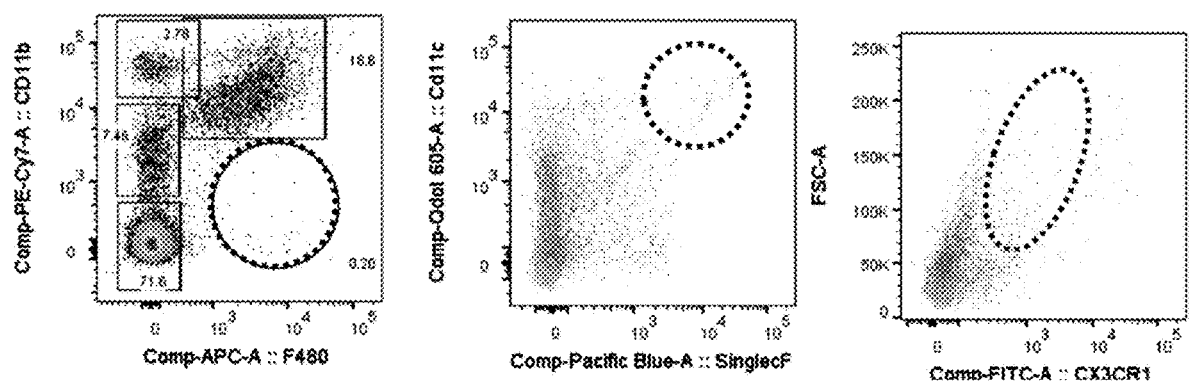
Figure 8C:
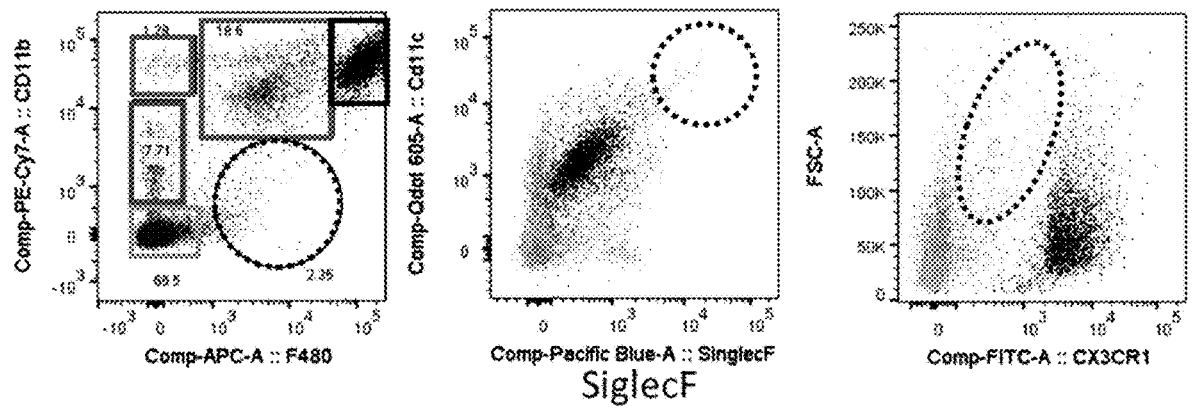

In this regard, the circled areas in FIGS. 8a, b and c show the presence or absence of alveolar macrophages, wherein alveolar macrophages are present in FIG. 8a and absent in FIGS. 8b and 8c. FIGS. 8a, b and c demonstrate that prior to intranasal transfer of ex vivo-derived macrophages, CSF2aR-KO mice are deficient in alveolar macrophages.

Figure 9:
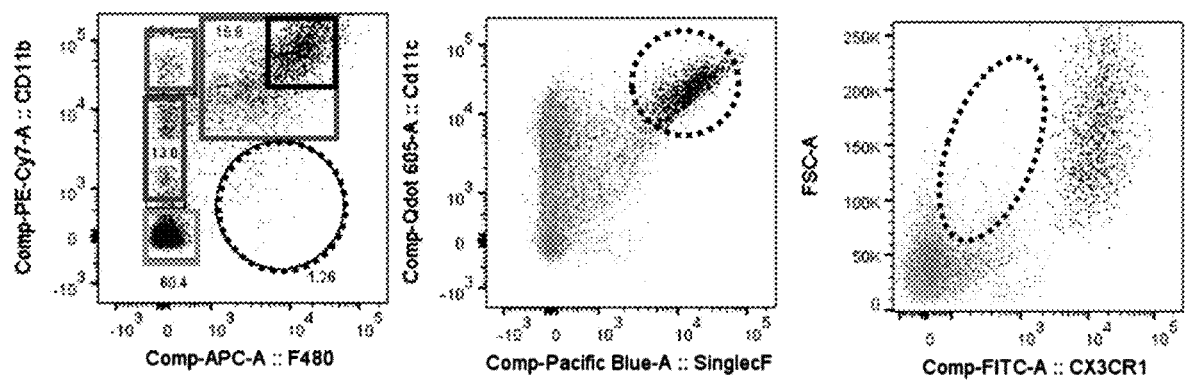
FIG. 9 shows the flow cytometry analysis of a CSF2aR-KO Mouse's lung (9-month-old) grafted with iPSC Mφ (1000K) for 42 Days. My refers to Macrophage.
Figure 10:
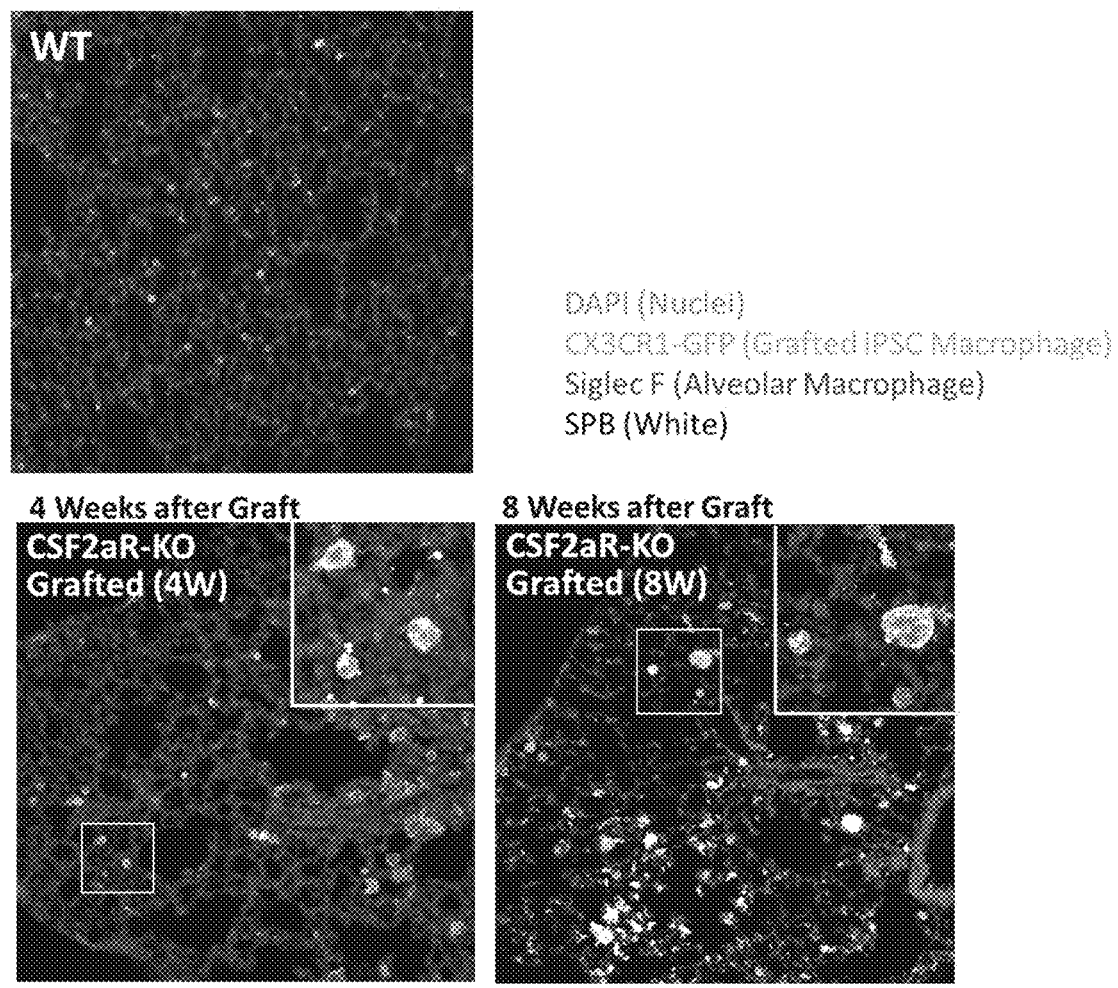
FIG. 10 shows that murine iPSC-derived primitive macrophages are able to engraft into the lung for more than 8 weeks and acquire markers of alveolar macrophages (SiglecF).

Moreover, in a further experiment the CSF2ar-KO mouse received intranasal transfer of 1000K iPSC CX3CR1-GFP macrophages, and cell suspensions of the lung were analysed by flow cytometry. As shown in FIGS. 9 and 10, murine iPSC-derived primitive macrophages (iPSC derived macrophages are F4/80 and CX3CR1-GFP and acquire Siglec-F expression) engraft into the lung for more than 42 days and acquire markers of alveolar macrophages (SiglecF) while concurrently maintaining the expression of specific markers such as CD11b. Specifically, the dotted circle in FIG. 9 represents the expected population of endogenous alveolar macrophages present in WT mouse.

Murine iPSC-derived primitive macrophages are also shown to engraft into the lung for more than 8 weeks and acquire markers of alveolar macrophages (SiglecF) and distribute into the whole lung (FIG. 10).

Figure 11:
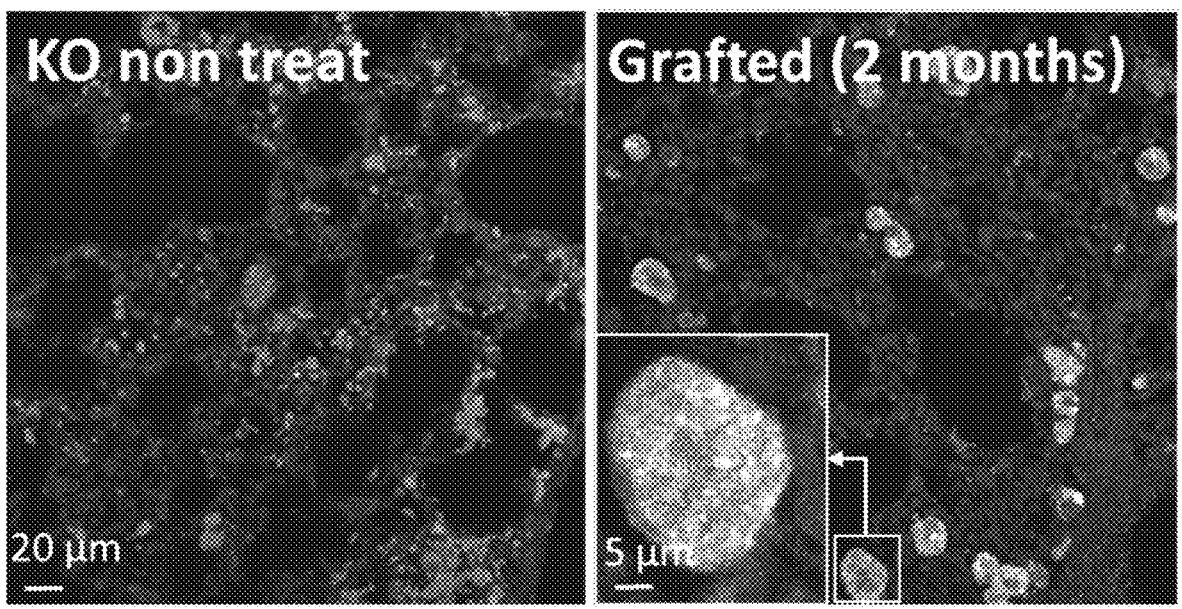
FIG. 11 shows that murine iPSC-derived primitive macrophages (CX3CR1-GFP+) may engraft into the lung for more than 8 weeks and phagocyte the Surfactant Associated Protein B (SPB).
Figure 12:
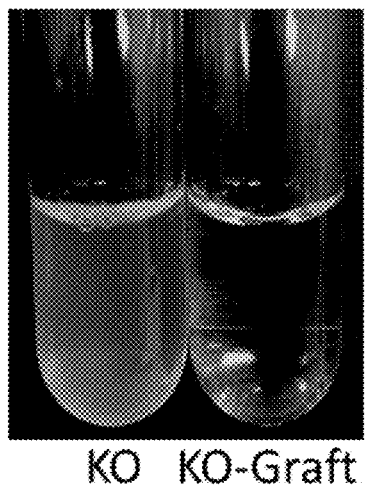
FIG. 12 shows the turbidity of the bronchoalveolar lavage fluid collected from CSF2aR-KO Mice (KO) and CSF2aR-KO Mice-grafted with iPSC-derived primitive macrophages (KO-graft). The optical density of the lavage fluid was measured at 600 nm.
Figure 12:
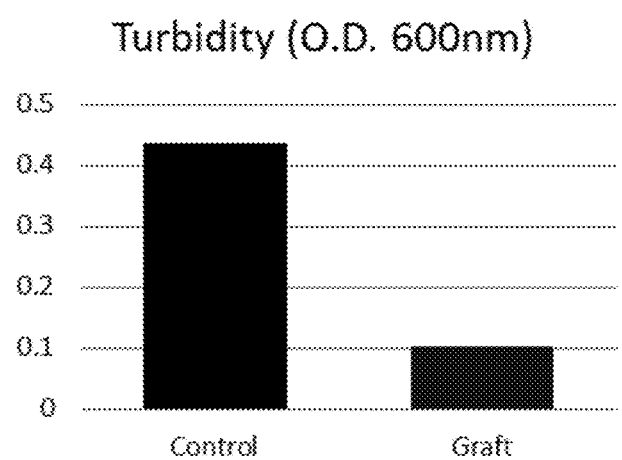
Figure 13:
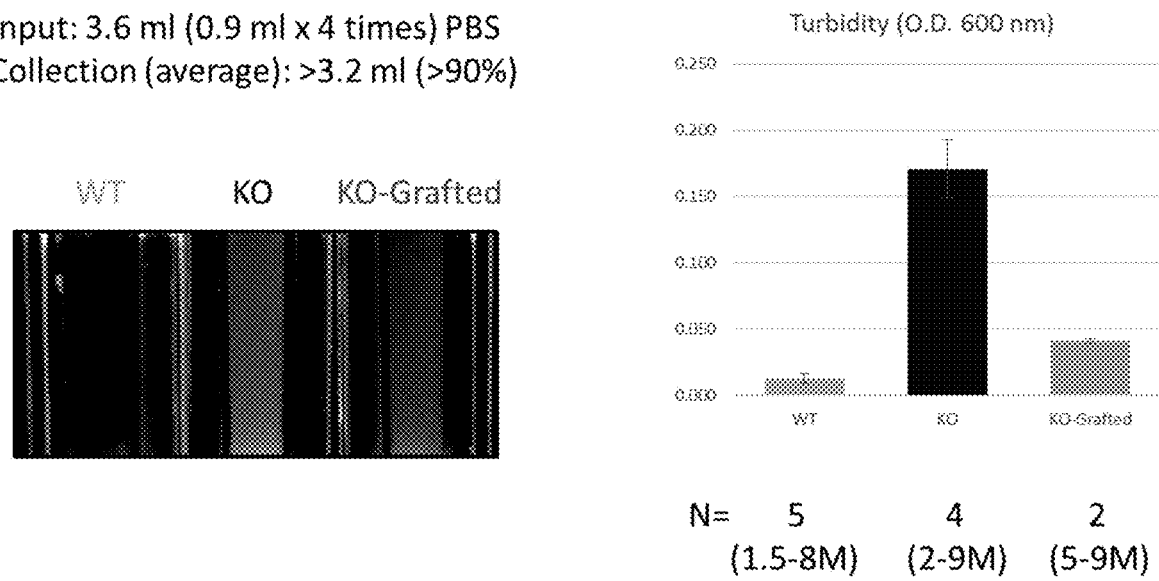
FIG. 13 shows the turbidity of the bronchoalveolar lavage fluid collected from wild type mouse (WT), CSF2aR-KO Mice (KO) and CSF2aR-KO Mice-grafted with iPSC-derived primitive macrophages (KO-graft). The optical density of the lavage fluid was measured at 600 nm.

Murine iPSC-derived primitive macrophages (CX3CR1-GFP+) were also shown to engraft into the lung for more than 8 weeks and phagocyte the Surfactant Associated Protein B (SPB) accumulated due to the absence of endogenous functional alveolar macrophages (See FIGS. 10 and 11). Consequently, there is less accumulation of SPB in the grafted lung and the turbidity of the bronchoalveolar measured by ELISA lavage is reduced (FIGS. 12 and 13). As will be appreciated, the effects and results shown on the CSF2aR-KO Mice (CD45.2) mouse model are a sign that the disease is cleared as a consequence of the treatment with iPSC-derived primitive macrophages.

What is claimed is:

1. A method for producing microglial cells, the method comprising:
(i)
(a) culturing human pluripotent cells in a serum-free culture medium comprising VEGF, BMP4 and a GSK3 inhibitor under normoxic conditions such that said pluripotent cells differentiate into cells of the mesoderm lineage;
(b) culturing said cells of the mesoderm lineage under hypoxic conditions in a culture medium comprising SCF, FGF-2, IL-3, IL-6, VEGF and DKK1 such that the cells of the mesoderm lineage differentiate into cells of the hematopoietic cell lineage;
(c) culturing said cells of the hematopoietic cell lineage in a culture media comprising SCF, FGF-2, IL-3 and IL-6 under normoxic conditions such that the cells of the hematopoietic cell lineage mature;
(d) culturing said mature cells of the hematopoietic cell lineage in a culture medium comprising M-CSF under normoxic conditions such that said mature cells of the hematopoietic cell lineage differentiate into primitive macrophages that express CD163, CD1 1b, HLA-DR, IBA-1, CX3CR1 and CD14;
(ii)
(a) culturing human pluripotent cells in neural progenitor cell (NPC) medium for up to 7 days such that neural precursor cells are obtained;
(b) culturing the neural precursor cells in NPC medium comprising a Rho-associated, coiled-coil containing protein kinase (ROCK) inhibitor;
(c) culturing the cells obtained in step (ii)(b) in NPC medium comprising epidermal growth factor (EGF) and basic fibroblast growth factor (bFGF);
(d) culturing the cells obtained in step (ii)(c) in neuronal differentiation medium such that neurons are obtained; and
(iii) culturing the primitive macrophages obtained in step (i)(d) with the neurons obtained in step (ii)(d) for up to 21 days such that microglial cells expressing ionized calcium binding adaptor molecule 1 (IBA1) are obtained.

2. The method of claim 1, wherein the NPC medium in step (ii)(b) comprises 10 µM ROCK inhibitor.

3. The method of claim 1, wherein the NPC medium in step (ii)(c) comprises 20 ng/ml EGF and 20 ng/ml bFGF.

* * * * *